(12) United States Patent  (10) Patent No.: US 7,013,706 B2
Tarumi  (45) Date of Patent: Mar. 21, 2006

(54) FRICTION FORCE MEASUREMENT APPARATUS

(75) Inventor: Ryohei Tarumi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/712,065

(22) Filed: Nov. 14, 2003

(65) Prior Publication Data

US 2004/0099059 A1    May 27, 2004

(51) Int. Cl.
*G01N 3/56* (2006.01)
(52) U.S. Cl. ............................................. 73/9
(58) Field of Classification Search .............. 73/788, 73/768, 763, 769, 774, 775, 9
See application file for complete search history.

(56) References Cited

U.S. PATENT DOCUMENTS 4,836,035 A * 6/1989 Tcheng et al. ........... 73/862.61

5,014,547 A * 5/1991 Holroyd ...................... 73/105

OTHER PUBLICATIONS

Seifert, H. (1998) Measuring frictional characteristics of video magnetic tapes-using test head simulating video head and drum mounted body. Derwent, DD 153231A.☐☐.*
Seifed, H. (1998) Measuring frictional charaderistics of video magnetic tapes-using test head simulating video mounted body. Derwent, DD 153231A (Translation).*

* cited by examiner

*Primary Examiner*—Max Noori
(74) *Attorney, Agent, or Firm*—Sughrue Mion, PLLC

(57) ABSTRACT

A friction force measurement apparatus which measure friction force between a fixed member fixed on a main body of a magnetic tape drive and a magnetic tape abrading the fixed member is characterized by being equipped with a vibration detector which is joined with the fixed member and a vicinity of the fixed member and detects vibration in abrasion of the magnetic tape with the fixed member, and a calculation device which calculates the friction force between the fixed member and the magnetic tape based on a signal from the vibration detector.

19 Claims, 1 Drawing Sheet

FRICTION FORCE MEASUREMENT APPARATUS

FIELD OF THE INVENTION

The present invention relates to a friction force measurement apparatus to measure friction force between a magnetic head and magnetic tape.

BACKGROUND OF THE INVENTION

As an index to evaluate runability of a magnetic tape, a measurement of friction force between a magnetic head and magnetic tape is widely performed and as a measuring method of running fiction of the magnetic tape, until now a following method has been adopted. In the method, firstly the magnetic tape is wound around a guide post of which material is same as that of a magnetic head, a weight is attached to one end of the magnetic tape, and on the other hand, a strain gauge is connected with the other end. Then, the strain gauge is pulled at a predetermined abrasion speed, tension at that time is measured by the strain gauge, and the friction force is calculated based on the tension.

However, although the conventional measurement method can calculate the friction force between the magnetic tape and guide post used instead of the magnetic head, it cannot accurately grasp the friction force between the magnetic head and magnetic tape practically running within a magnetic drive. In this connection, to handle this problem, there conventionally exists a measurement device to measure the friction force between the magnetic head and magnetic tape practically running within the magnetic drive by detecting a torque burdening a rotation shaft of a rotation head (for example, see FIG. 3 in Japan patent laid open publication 05-187993). However, the measurement device cannot be utilized for measuring the friction force within the magnetic tape drive with an unrotating head.

SUMMARY OF THE INVENTION

A exemplary object of the present invention is to provide a friction force measurement apparatus which can favorably measure friction force between a magnetic head and magnetic tape even within a magnetic tape drive with an unrotating head A first a of friction force measurement apparatus of the invention is an apparatus to measure the friction force between a fixed member fixed on a main body of a magnetic tape drive and a magnetic tape abrading the fixed member: the apparatus is characterized by being equipped with a vibration detector which is joined with the fixed member and its vicinity, and detect a vibration in abrasion of the magnetic tape with the fixed member; and a calculation device which calculates the friction force between the fixed member and magnetic tape based on a signal from the vibration detector.

Here, the "fixed member" means a something which is fixed on the main body of the magnetic tape drive and has a portion abrading the magnetic tape. For example, as the fixed member, there exist a fixed head, guide portion guiding both ends in a width direction of the magnetic tape, guide roller, and the like.

According the first aspect of apparatus of the invention, when making the magnetic tape run by driving the magnetic tape drive, the vibration occurring between the magnetic tape and fixed member is detected by the vibration detector, and the signal is sent to the calculation device. Then, based on the signal, the calculation device calculates the friction force between the magnetic tape and fixed member.

A second aspect of apparatus of the invention is characterized, in the constitution of the lint aspect, that a vibration input unit being an input portion of vibration of the vibration detector is made to directly contact the fixed member.

According to the second aspect of apparatus of the invention, in addition to the action of the first aspect, the vibration input unit of the vibration detector is made to directly contact the fixed member, and other portions are made to be fixed on the fixed member with, for example, an adhesive and the like. Then, when the magnetic tape drive is driven, the vibration, which occurs from the fixed member contacting a running magnetic tape, results in directly being transmitted to the vibration input unit of the vibration detector without being intervened by the adhesive and the like.

A third aspect of apparatus of the invention is characterized, in the constitution of the first aspect and second aspect, by being equipped with a low pass filter of which cutoff frequency is not less than 50 kHz between the vibration detector and calculation device.

According to the third aspect of apparatus of the invention, in addition to the action of the first aspect and second aspect, when the low pass filter of which cutoff frequency is, for example, 50 kHz is used, signals not less than 50 kHz out of those output from the vibration detector are attenuated (cut).

A fourth aspect of apparatus of the invention is characterized, in any one of the constitution of the first aspect to third aspect of the invention, by being equipped with a recording device recording the friction force calculated by the calculation device with time.

According to the fourth aspect of apparatus of the invention, in addition to the action of any one of the first aspect to the third aspect of the invention, the friction force calculated by the calculation device is recorded in the recording device with time. That is, in the recording device, a change of the friction force over time results in being recorded.

DESCRIPTION OF THE PREFERRED EMBODIMENTS

Figure 1:
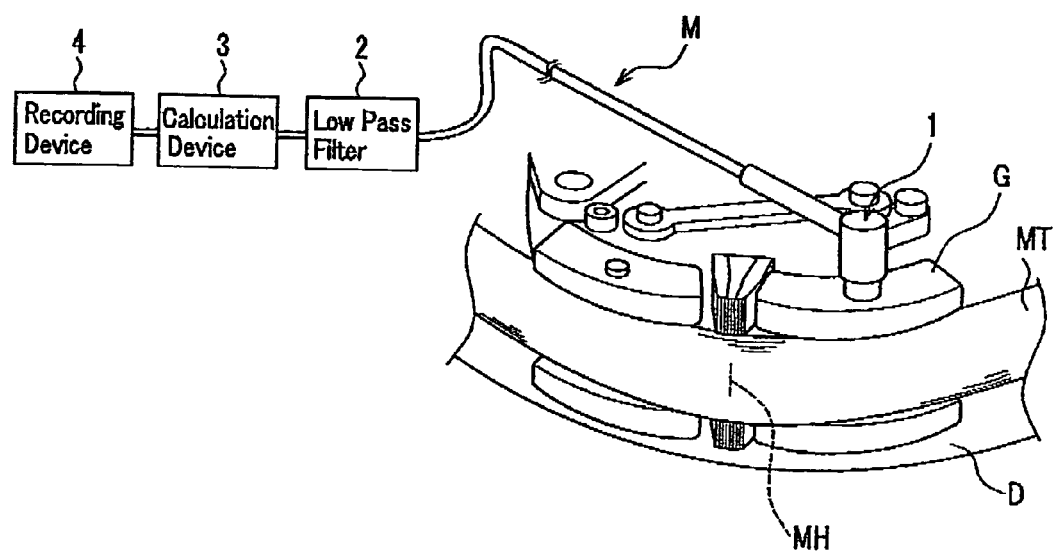
FIG. 1 is a configuration drawing showing a friction force measurement apparatus related to the invention

Hereinafter, the friction force measurement apparatus related the present invention will be described in detail, referring to the drawings, As shown in FIG. 1, a fiction force measurement apparatus M is an apparatus to measure the fiction force between a magnetic head (fixed member) MH fixed on a main body of a magnetic tape drive D and a magnetic tape MT abrading the magnetic head MH. The friction force measurement apparatus M is mainly composed of an AE (Acoustic Emission) sensor 1, low pass filter 2, calculation device 3, and recording device 4. Here, the AE sensor 1 outputs a minute vibration converting to a current or voltage.

Figure 2:
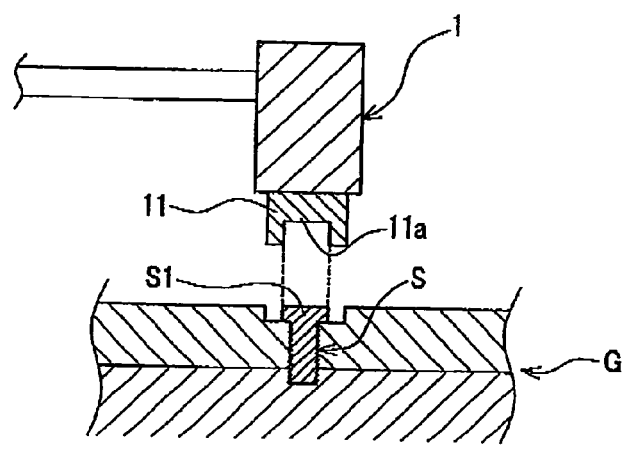
FIG. 2 is a section drawing showing an attached stricture of an AE sensor.

The AE sensor 1 is a device to detect a vibration when the magnetic tape MT abrades with the magnetic head MH and is joined with a guide portion (fixed member) G guiding end portion in a width direction of the tape MT unifiedly fixed on the head MH. To be more precise, the sensor 1 is formed, as shown in FIG. 2, as a cylindrical shape with a bottom where its lower portion 11 opens downward and an inner diameter of the portion 11 is formed as approximately same largeness as that of outer diameter of head portion S1 of a screw (fixed member) S to fix each member of the guide portion G. In addition, a bottom portion 11a of the portion 11 which is the cylindrical shape with the bottom is a vibration input unit being a portion where a vibration is input. Then, by pressing (fitting in) the lower portion 11 into the head portion S1 of the screw S by hand, the bottom portion 11a which is the vibration input unit results in directly contacting the screw S.

A low pass filter 2 of which cutoff frequency is 50 kHz attenuates (cuts) signals not less than 50 kHz out of those output from the AE sensor 1. That is, the low pass filter 2 focuses many kinds of signals output from the AE sensor 1 on specific signals derived from friction between the head MH and tape MT. Meanwhile, as the cutoff frequency, it is desirable to select 50 to 300 kHz.

A calculation device 3 calculates the friction force between the head MH and tape MT based on signals passing through the filter 2. Data showing the friction force calculated by the calculation device 3 is output in a recording device 4.

The recording device 4 records the friction force calculated by the calculation device 3 with time. That is, the recording device 4 correspondingly records the data showing the friction force output from the calculation device 3 and time when the data is input, thereby recording the change of the friction force over time occurring between the head MH and tape MT.

Next, a friction force measuring method using the friction force measurement apparatus M is described As shown in FIG. 1, after setting a magnetic tape cartridge not shown in the drawing in the magnetic tape drive D, drive the tape drive D, thereby running the tape MT. Then, the measurement apparatus M is also actuated together, the AE sensor 1 detects a vibration occurring between the head MH and running tape MT, and signals of the AE sensor 1 are output in the calculation device 3 through the filter 2. And the data show the friction force calculated by the calculation device 3 is output in the recording device 4, and the data is recorded with time by the device 4, thereby resulting in the change of the function force over time being recorded. That is, the measurement apparatus M measures the friction force by measuring the vibration.

Thus, in the embodiment, following effects can be obtained.

1. Because the fiction force measurement apparatus M calculates the fiction force between the magnetic head MH and magnetic tape MT, even within a magnetic tape drive with an unrotational magnetic head a friction measurement between a magnetic head and magnetic tape within the drive can favorably be performed
2. Because a vibration from the head MH is directly transmitted to the bottom portion 11a which is the vibration input unit of the AE sensor 1 through the screw S, the AE sensor 1 can surely detect the vibration.
3. Because signals with frequencies not less than 50 kHz are cut by the low pass filter 2 of which cutoff frequency is 50 kHz, many kinds of signals output from the AE sensor 1 can be focused on the specific signals derived from the friction between the head MH and tape MT.
4. Because the charge of the friction force over time occurring between the head MH and tape MT is recorded in the recording device 4, a friction phenomenon within the magnetic tape drive D can be analyzed in more detail.

Meanwhile, the invention is not limited to the embodiment and is practiced in various patterns.

Although the embodiment attaches the AE sensor 1 around the screw S which is one of members of the guide portion G, the invention is not limited to this, and the AE sensor 1 may be directly attached to the head MH and be attached to other members such as a guide roller contacting the tape MT. Moreover, because the vibration of a portion contacted with the tape MT may be detected by the AE sensor 1, in case of a position which is a vicinity of the contacted portion and at which the vibration can be detected, the AE sensor 1 may be attached to the main body of the apparatus. However, the method attaching the AE sensor 1 around the screw S like the embodiment enables the AE sensor 1 to be easily attached only by appropriately providing a measured objective with the screw S in which the head S1 can fit in the lower portion 11 being the cylindrical shape with the bottom of the AE sensor 1.

On the other hand, to attach the AE sensor 1 by a press fit, the screw S need not be always provided. For example, to provide a fix member such as the fixed head with a protrusion portion formed in a diameter which can fit in the lower portion 11 of the AE sensor 1 also makes it possible to insert the sensor 1 in the protrusion portion as freely detachable/attachable.

Meanwhile, an attaching method of the AE sensor 1 is arbitrary selectable, and for example, forming a flange at a side surface of the sensor 1, the flange may be joined with the fixed member with a screw, adhesive, and the like. In addition, for example, by cutting a female screw thread on an inner circumference surface of the lower portion 11 which is the cylindrical shape with the bottom, the AE sensor 1 may be made to be attached to a male screw portion provided at a measured objective by screwing-in. However, because the method pressing the AE sensor 1 into the screw S by hand like the embodiment enables its detachment/attachment to be easily performed, it is preferable to be attached by such the method.

What is claimed is:

1. A friction force measurement apparatus which measures friction force between a fixed member fixed on a main body of a magnetic tape drive and a magnetic tape abrading the fixed member, the apparatus comprising:
    a vibration detector which is joined with said fixed member and detects a vibration in abrasion of said magnetic tape with said fixed member; and
    a calculation device which calculates the friction force between said fixed member and said magnetic tape based on a signal from said vibration detector,
    wherein said fixed member is a guide portion regulating a width direction of a magnetic tape.

2. A friction force measurement apparatus according to claim 1, wherein a vibration input unit in which vibration of said vibration detector is input is directly contacted with said fixed member.

3. A friction force measurement apparatus according to claim 1, wherein a low pass filter having a cutoff frequency of not less than 50 kHz is disposed between said vibration detector and said calculation device.

4. A friction force measurement apparatus according to claim 2, wherein a low pass filter having a cutoff frequency of not less than 50 kHz is disposed between said vibration detector and said calculation device.

5. A friction force measurement apparatus according to claim 1, wherein a recording device records the friction force calculated by said calculation device and records a time associated with the friction force calculated by said calculation device.

6. A friction force measurement apparatus according to claim 2, wherein a recording device records the friction force calculated by said calculation device and records a time associated with the friction force calculated by said calculation device.

7. A friction force measurement apparatus according to claim 2, wherein said vibration detector is pressed into a head of a screw.

8. A friction force measurement apparatus according to claim 1, wherein said fixed member is a magnetic head.

9. A friction force measurement apparatus according to claim 3, wherein said vibration detector is pressed into a head of a screw.

10. A friction force measurement apparatus according to claim 1, wherein said vibration detector is an acoustic emission sensor.

11. A friction force measurement apparatus which measures friction force between a fixed member fixed on a main body of a magnetic tape drive and a magnetic tape abrading the fixed member, the apparatus comprising:
a calculation device which calculates the friction force between said fixed member and said magnetic tape based on a signal from said vibration detector,
wherein said vibration detector is pressed into a head of a screw.

12. A friction force measurement apparatus according to claim 11, wherein a vibration input unit in which vibration of said vibration detector is input is directly contacted with said fixed member.

13. A friction force measurement apparatus according to claim 11, wherein a low pass filter having a cutoff frequency of not less than 50 kHz is disposed between said vibration detector and said calculation device.

14. A friction force measurement apparatus according to claim 12, wherein said fixed member is a guide portion regulating a width direction of a magnetic tape.

15. A friction force measurement apparatus according to claim 13, wherein said fixed member is a guide portion regulating a width direction of a magnetic tape.

16. A friction force measurement apparatus according to claim 12, wherein a low pass filter having a cutoff frequency of not less than 50 kHz is disposed between said vibration detector and said calculation device.

17. A friction force measurement apparatus according to claim 11, wherein said fixed member is a magnetic head.

18. A friction force measurement apparatus according to claim 11, wherein said vibration detector is an acoustic emission sensor.

19. A friction force measurement apparatus according to claim 11, wherein a recording device records the friction force calculated by said calculation device and records a time associated with the friction force calculated by said calculation device.

* * * * *